(12) United States Patent
Nomura et al.

(10) Patent No.: US 7,449,159 B2
(45) Date of Patent: Nov. 11, 2008

(54) LIQUID PROCESSING DEVICE AND METHOD OF MANUFACTURING PROCESSED LIQUID

(75) Inventors: Syuushi Nomura, Osaka (JP); Aoi Kawasaki, Kyoto (JP)

(73) Assignee: Wellness Co., Ltd, Osaka-shi (JP)

( * ) Notice: Subject to any disclaimer, the term of this patent is extended or adjusted under 35 U.S.C. 154(b) by 446 days.

(21) Appl. No.: 10/500,042

(22) PCT Filed: Dec. 24, 2002

(86) PCT No.: PCT/JP02/13473

§ 371 (c)(1),
(2), (4) Date: Jun. 23, 2004

(87) PCT Pub. No.: WO03/055591

PCT Pub. Date: Jul. 10, 2003

(65) Prior Publication Data

US 2005/0121811 A1    Jun. 9, 2005

(30) Foreign Application Priority Data

Dec. 25, 2001    (JP)    ............................. 2001-391036

(51) Int. Cl.
   *B01J 19/24*    (2006.01)
   *B01J 19/26*    (2006.01)
   *B01F 5/06*    (2006.01)

(52) U.S. Cl. ...................... 422/224; 422/227; 422/229; 138/42; 138/44; 366/336; 366/339; 261/23.1

(58) Field of Classification Search ................. 366/336, 366/337, 338, 339, 340; 261/23.1, 34.1; 422/224, 227, 229
See application file for complete search history.

(56) References Cited

U.S. PATENT DOCUMENTS 2,466,684 A * 4/1949 Case .......................... 165/148
2,793,835 A * 5/1957 Woods ........................ 165/148

(Continued)

FOREIGN PATENT DOCUMENTS

DE    38 27 317    2/1990

(Continued)

OTHER PUBLICATIONS

Suplemental European Search Report for application No. EP 0278602, search in Munich, completed on Mar. 2, 2005, 2 pages.*

(Continued)

*Primary Examiner*—Tony G Soohoo
(74) *Attorney, Agent, or Firm*—Westerman, Hattori, Daniels & Adrian, LLP.

(57) ABSTRACT

The present invention also relates to a fluid processing device using material pieces, which is usable for processing liquid and gas. The hexagon nut shaped material pieces of stainless steel and the like are heat-treated and oriented such that the material pieces form up into a kind of concentric circles and make single plane, with drawing lines linked the center points of the hexagonal nut shaped material pieces positioned the outermost circumferentially periphery of the concentric arrangement forming up into an equilateral hexagon and such arrangement is retained. Also, a fluid processing device comprises a hollow container that such field converter is positioned in.

10 Claims, 4 Drawing Sheets

U.S. PATENT DOCUMENTS

| | | | | |
|---|---|---|---|---|
| 3,089,683 | A | * | 5/1963 | Adams et al. ............... 366/340 |
| 3,265,128 | A | * | 8/1966 | Legrand ..................... 165/159 |
| 3,424,437 | A | * | 1/1969 | Shearer ...................... 366/339 |
| 3,747,656 | A | * | 7/1973 | Mortus ....................... 411/281 |
| 4,208,136 | A | * | 6/1980 | King .......................... 366/338 |
| 4,806,288 | A | * | 2/1989 | Nowosinski et al. .......... 261/94 |
| 4,811,786 | A | * | 3/1989 | Kamilos et al. ............. 166/303 |
| 4,867,233 | A | * | 9/1989 | Gemeinhardt ............... 165/173 |
| 5,304,423 | A | | 4/1994 | Niknafs et al. |
| 5,605,400 | A | * | 2/1997 | Kojima ....................... 366/339 |
| 7,240,723 | B2 | * | 7/2007 | Wu et al. .................... 165/158 |
| 2004/0076563 | A1 | | 4/2004 | Kitada |

FOREIGN PATENT DOCUMENTS

| | | | |
|---|---|---|---|
| DE | 100 00 345 | | 5/2000 |
| EP | 1462163 | * | 9/2004 |
| JP | 01-242837 | | 9/1989 |
| JP | 01242837 | * | 9/1989 |
| JP | 1219/1990 | | 1/1990 |
| JP | 3-87129 A | | 4/1991 |
| JP | 6-312191 A | | 11/1994 |
| JP | 07-004084 | | 1/1995 |
| JP | 7-47140 A | | 2/1995 |
| JP | 7-206617 A | | 8/1995 |
| JP | 8-281027 | | 10/1996 |
| JP | 08281027 | * | 10/1996 |
| JP | 09-010776 | | 1/1997 |
| JP | 9-10871 A | | 1/1997 |
| JP | 09010776 | * | 1/1997 |
| JP | 2000-248302 A | | 9/2000 |
| WO | WO 02/060576 A1 | | 8/2002 |

OTHER PUBLICATIONS

"Drive Ya Nuts by Milton Bradley—Sam's Toybox", Http:///www.samstoybox.com/toys/DriveYaNuts.html, 4pgs, as printed on Jan. 5, 2008.*

Picture of Drive Ya Nuts puzzle product, travel edition, made in late 1980s shown in web page http://www.powerstrike.net/puzzles/pics/maths_drive_ya_nuts.jpg as printed on Jan. 5, 2008, 1 page.*

Picture of Thinkominos puzzle product, shown in web page http://www.powerstrike.net/puzzles/pics/maths_think_ominos.jpg as printed on Jan. 5, 2008, 1 page.*

Japanese Office Action dated Sep. 13, 2007, issued in corresponding Japanese application No. 2003-556163.

* cited by examiner

LIQUID PROCESSING DEVICE AND METHOD OF MANUFACTURING PROCESSED LIQUID

FIELD OF THE INVENTION

The present invention relates to a liquid processing device comprising an arrangement of material pieces of which shape is a hexagonal prism. Further, the present invention relates to a method of manufacturing processed liquid which utilizes the liquid processing device.

BACKGROUND ART

As a space that improves vitality of human beings, Japanese Patent Laid-Open No. H7-4084 disclosed treatment room for patients, which is surrounded with boards having through-holes of hexagonal shape.

The above mentioned treatment room needs large capacity surroundings for the space expecting conversion and also big facilities. In addition they require significant labor to make.

It is an object of this invention to obtain a liquid processing device that is capable of converting processing liquid into suitable one for human beings, animals and plants. Other object of this invention is to provide a method of manufacturing processed liquid, which is suitable one for human beings, animals and plants.

SUMMARY OF THE INVENTION

An embodiment of the present invention is a liquid processing device. The liquid processing device comprises a container and arrangement(s) of hexagonal material pieces. In this specification, "arrangement of hexagonal material pieces" abbreviates as "arrangement of pieces."

First, arrangement of pieces is explained.

(Arrangement of Pieces)

The arrangement of pieces comprises a certain number of material pieces having an external shape of an equilateral hexagonal prism, oriented in an arrangement such that the central axes thereof are parallel with each other, and this arrangement is retained. In the present invention and in this specification, the central axis means an axis that is parallel to six sides of the equilateral hexagonal prism and perpendicular to the base and top of both sides of the equilateral hexagonal prism.

An example of this material piece is a hexagon nut. Namely, the material piece has a hole penetrating through the top and the base. The hole has an annular section. Also, the hole has a spiral groove on the internal surface thereof. Material of the material piece is austenitic stainless steel, martensitic stainless steel, platinum, gold, silver, titanium or diamonds. Also, the material piece is heat-treated.

This material piece itself has the ability of liquid conversion. Because such plural material pieces are oriented in the same direction, and retain this arrangement, the liquid conversion abilities of the plural material pieces composing the arrangement of pieces are gathered and cooperate with each other.

With regard to the arrangement of pieces, the certain number of material pieces may have the same shape and same size as each other, and holes having a circular prism shape with a central axis which is identical with the central axis of the overall material piece. Also, concerning the arrangement of the plural material pieces, the bases of the plural material pieces make one imaginary plane, and the sides of the material pieces are adjacent to each other. Because the material pieces are arranged with the sides of material pieces adjacent to each other, the ability of liquid conversion of the material pieces concentrates so that the ability of the arrangement of pieces becomes stronger.

In the present invention, the phrase "sides of the material pieces adjacent to each other" means the distance between the center of two material pieces put side by side in the arrangement, is equal to or less than 3 times the length (l) of one side of a cross section of the equilateral hexagon prism thereof. In addition, the phrase includes both the arrangement wherein the sides of the material pieces come close each other and the arrangement wherein the sides of material pieces touch each other.

The arrangement of pieces may be such that, the material pieces therein are formed into kind of concentric circle, and a drawing line linked projected points, which are caused that the central axis of the outermost circumferentially located plural material pieces of said kind of concentric circle are projected to a imaginary plane which is perpendicular to the axis of the material piece, forms into an equilateral hexagon. Because the plural material pieces are arranged in concentric equilateral hexagon, the ability of liquid conversion of the material pieces becomes more concentration. Therefore, the ability of the arrangement of pieces becomes stronger.

In the present invention, if the material pieces are oriented in an arrangement having a level surface, a drawing line linked center points of the material pieces of the outermost circumferentially located plural material pieces, forms into an equilateral hexagon. If the material pieces are oriented in an arrangement having an uneven surface, a drawing line linked projected points, which are caused that the central axes of the outermost circumferentially located plural material pieces of said kind of concentric circle are projected to an imaginary plane which is perpendicular to the axis of the material piece, forms into an equilateral hexagon. The expression of the imaginary plane "which is perpendicular to the central axis of the material piece" can be expressed, in other words, the imaginary plane "which is parallel to the base of the material piece".

The arrangement of pieces may comprise a plurality of the arrangement of pieces as explained above, wherein these arrangements of pieces are piled one on top of the other. Because the number of material pieces increases, the ability of the arrangement of pieces becomes stronger.

The arrangement of pieces may comprise a plurality of the arrangement of pieces are piled such that, one on top of the other, and central axes of the central material pieces of said kind of concentric circle arrangement thereof, are generally aligned. Because plural center of the equilateral hexagons of the material pieces align, the ability of the arrangement of pieces becomes stronger.

With regard to the arrangement of pieces, material of the material piece may comprise SUS304 stainless steel. According to the invention, a nut of SUS304 stainless steel which is an article on the market, can be employed as the material piece. Therefore, the arrangement of pieces is provided at lower price.

With regard to the arrangement of pieces, the material pieces may be heat-treated in a heating temperature equal to or more than 800° C., for a duration equal to or more than 5 minutes. By heat-treating in this range, the ability of the arrangement of pieces becomes stronger.

With regard to the arrangement of pieces, the length of a side of the equilateral hexagon being designated as a cross section of the equilateral hexagonal prism of the material piece, may be equal to or less than 10 mm, and the height of the equilateral hexagonal prism may be shorter than the length of the side. When a material piece of this size range is utilized, the ability of the arrangement of pieces becomes stronger.

With regard to the arrangement of pieces, the spiral groove of the internal perimeter surface of the hole of the material piece may have a triangle screw shape. A spiral groove of this shape can be manufactured cheaply. As a result, the arrangement of pieces can be obtained at lower cost.

Figure 1:
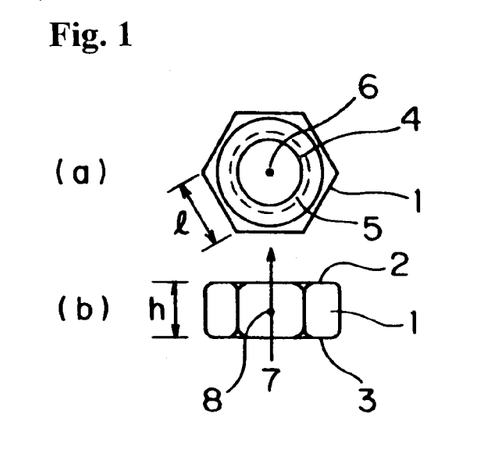
FIG. 1 is a surface view (a) and a side view (b) of the material piece.

The material piece using the present invention is explained as follows. FIG. 1 (a) is a surface view of a material piece and (b) is a front view of a material piece. The material piece 1 is equal to a hexagon nut in shape. Namely, the external shape of material piece 1 is an equilateral hexagonal prism. A top and a base of the material piece 1 may be finished with chamfering or without chamfering. FIG. 1 shows the shape with chamfering.

The material piece 1 has a hole 4 having annular section, penetrating through a top 2 and a base 3. The hole may be a normal circular prism or inclined circular prism. The inclined circular prism means both ends (i.e. the top and base of the material piece) are parallel and both ends are not perpendicular to a central axis of the prism. The normal circular prism is preferable.

In addition, the hole may be positioned in a center of the equilateral hexagonal prism or in an eccentric location. The hole positioned in a center is preferable. Because the material piece shown in FIG. 1 has the hole positioned in a center of the equilateral hexagonal prism (i.e., external shape of the material piece), a central axis 7 of the hole 4 is equal to the central axis 7 of the equilateral hexagonal prism. A point 6 shows the projection point of the central axis 7. A spiral groove 5 is carved within the internal perimeter surface of the hole 4. A point 8 is a projection point of center point of material piece 1. As described above, the point 6 is a projection point of central axis 7, also, the point 6 is a projection point of center point of the material piece 1.

Material of the material piece 1 is chosen from austenitic stainless steel, martensitic stainless steel, platinum, gold, silver, titanium or diamond. Austenitic stainless steel is an alloy of iron 72%, nickel 8%, chrome 18% and other metallic elements, and includes SUS304, SUS316, SUS303, SUS301, SUS302, SUS201 and the like. Martensitic stainless steel is an alloy of iron 85%, chrome 13% and other metallic elements, and includes SUS410, SUS416, SUS420J2, and the like. Diamond includes natural diamond and synthetic diamond.

Preferable material of the material piece is austenitic stainless steel, martensitic stainless steel, and titanium, more preferable material is austenitic stainless steel, and particularly preferable material is SUS304, from the viewpoint of procurement with lower cost.

The material piece 1 gains the ability of liquid conversion by heat-treating. The temperature for heat-treating the material piece 1 is generally equal to or more than 800° C., preferably 900-1500° C., particularly preferably 1000-1200° C. However, the heat-treating is made below the melting point temperature of the material of the material piece 1.

Duration of the heat-treatment is generally equal to or more than 5 minutes, preferably equal to or more than 10 minutes, more preferably 10-120 minutes, particularly preferably 30-90 minutes. The combination of temperature and duration of the heat-treatment, is preferably 1000-1200° C. and 30-90 minutes. Cooling time after heat-treating does not have a particular requirement. Therefore cooling under room temperature can be done. Passivation may or may not be done to stainless steel after heat-treating.

The size of the material piece 1 is not limited in particular. However, length of one side (arrow 1 in FIG. 1) of the equilateral hexagon is generally equal to or less than 10 mm, and preferably equal to or less than 6 mm, more preferably equal to or less than 5 mm. Also, height (arrow h in FIG. 1) of the material piece 1 does not have any limit in particular. However, the height h is generally equal to or less than the length of one side 1, preferably equal to or less than 1×0.85.

The number of circlings of the spiral groove carved within the internal perimeter surface of the hole of the material piece 1 is equal to or more than one. There is no upper limit for the number of circlings of the spiral groove in particular. The depth of the spiral groove does not have any limit in particular.

The shape of the groove is expressed as the shape of the screw thread. A groove having a triangular screw thread or a screw thread of trapezoidal shape can be used. The triangular screw thread includes the thread having an angle of 60 degrees, of 55 degrees, and the like. Triangular screw thread is preferable from the viewpoint of lower price and easy procurement.

The arrangement of the material piece 1 is explained, as follows. The arrangement of pieces of the present invention is that the plural material pieces are oriented such that the central axis (7 of FIG. 1) of each material piece is parallel to each other. In other words, each of the bases of the plural material pieces becomes parallel with one imaginary plane. The plural material pieces may be oriented such that the material pieces are uneven in relation to each other. Or, they may be oriented such that the plural bases of the material pieces make a single imaginary plane. The preferred arrangement is the arrangement such that the plural bases of the material pieces make a single imaginary plane.

The plural material pieces that are employed in a single arrangement of pieces may be any of the following:

(i) the outside dimension of each material piece is different from each other;

(ii) the outside dimension of each material piece is the same, and size of each of the holes of each material piece is different from each other;

(iii) the outside dimension and the size of the hole of each material piece is the same, and the shape of the internal spiral groove for each material piece is different from each other; or (iv) the size and the shape are the same for each material piece. The preferred is (iv).

The plural material pieces can be oriented so as to have distance between the material pieces, or have the material pieces adjacent to one another or be in contact with each other in a single arrangement. The preferable arrangement is having adjacent material pieces, and the more preferable arrangement is having the material pieces being in contact with each other. The arrangement pattern can be an arbitrary pattern such as a random arrangement, a lattice-shaped arrangement, and a kind of concentric circle arrangement.

Figure 2:
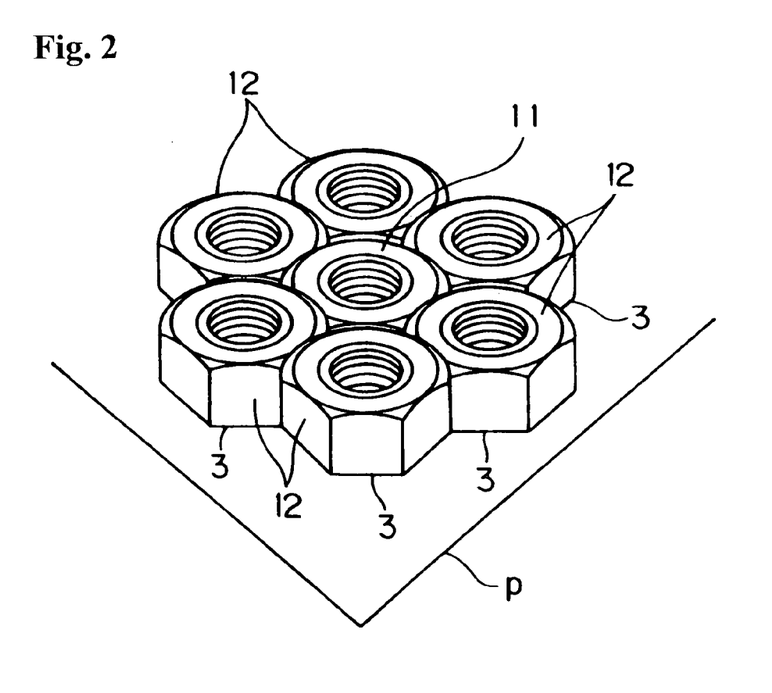
FIG. 2 is a perspective view showing an example of the arrangement of the material pieces.

FIG. 2 is a perspective diagram showing an example of the arrangement of the material pieces. It shows a kind of concentric circle arrangement. Plural material pieces 1 are oriented in the shape of a plane, and bases 3 of the material pieces 1 make one imaginary plane p. A material piece 11 is put in the center of the arrangement, and six material pieces 12 are oriented in the circumference. A drawing line linked the center points of the material pieces 12 put in the outermost circumference, forms up into an equilateral hexagon. Such equilateral hexagonal arrangement is hereinafter called OHA (Orthodox-Hexagonal Arrangement).

In FIG. 2, seven in total of the material pieces are employed in OHA. However, more circumference can be added, in such cases the total number of the material pieces employed are 19, 37, 61, 91, 127 - - - .

In addition, the concentric circle arrangement includes the arrangement such that three material pieces are oriented at a most inner circumference. In such case, a drawing line linked the center of the material pieces put in the outermost circumference, forms up into an equilateral triangle. Preferred arrangement is OHA.

The present invention comprises the arrangement of the material piece in a single plane. However, a single arrangement of pieces can be made such that the arrangements are stacked one on top of the other. The number of stacks does not have any limit in particular, and an arbitrary number of arrangements in the single plane can be stacked up. The preferable stacked-up pattern is such that the constituent arrangements have OHA, and the center point of each OHA is aligned in the top and base direction. In other words, the stacked-up pattern is such that the central axes 7 of the material piece 1 placed in the center of each arrangement form an imaginary single straight line. The imaginary straight line of the central axes 7 formed becomes approximately straight when in order to hold a stacked-up pattern, a box which receives the material pieces with some differential margin, is employed.

The preferable stacked-up pattern, includes a stacked-up pattern of one to accord with an equilateral hexagon up and down, and a twisted equilateral hexagon of the OHAs. The most preferable stacked-up pattern is the one to accord with an equilateral hexagon up and down.

In order to hold the arrangement, various kinds of well-known structures and methods can be employed. The example of such structures and methods are as follows:

A structure to pack the material pieces into a box having a shape of an equilateral hexagonal prism so that the material pieces are oriented into the above-mentioned arrangement, and to cover the box of top and base with lids;

A structure to orient the material pieces in a box of which the particular shape is not required, and to fill filling up materials in the gap of the box so that the material pieces are pressed from upside, bottom, right and left thereof, consequently the arrangement is held;

A structure to fix the plural material pieces to a bolt, and to fix such plural bolts with a tool for unity;

A method to fix material piece with adhesive on a board; and

A method to fix material pieces with adhesive to each other.

When structure to pack the material pieces into a box is adopted, there may be some differential margin between a box and material pieces. Or, there may be no differential margin. If there is some differential margin, a work to pack the material pieces into the box becomes easy.

The arrangement of pieces of the present invention can be used as the form of the arrangement itself, or it can be used as packed in a container. Material of the container is not any limit in particular. For example, container made of metal, synthetic resin, glass, wood and the like can be employed. Container made of metal is preferable, in the light of easy forming and durability, stainless steel is more preferable, in the light of being rust proof, SUS304 is particularly preferable in the light of easy procurement.

The container may be sealed or opened to outside. It is preferable to be sealed in the light of avoiding dust.

(Liquid Processing Device)

The liquid processing device that is one embodiment of the present invention is explains as follows.

The liquid processing device comprises a hollow container having an intake and an outlet, wherein the arrangement of pieces is positioned in said container. In the liquid processing device, processed liquid passes close to the arrangement of pieces. Therefore, the liquid processing device can change the nature of the processed fluid.

Shapes of the hollow container include, for example, a hollow column shape (e.g. a column, a quadratic prism, etc.) and a funnel shape. The liquid includes solution, suspension, colloidal solution, mixture with liquid and particles. The material of the hollow container is not limited in particular. For example, metal, synthetic resin, glass, wood and the like can be employed. Metal is preferable, in the light of easy forming and durability. Stainless steel is more preferable, in the light of being rust proof. SUS304 is particularly preferable in the light of easy procurement.

The hollow container may be equipped with a distinguishable intake and outlet, or may be equipped with two entrances, one of which is used as an intake, and the other is used as an outlet.

With regard to the liquid processing device, the central axes of the material pieces being constituent of the arrangement of pieces, may be generally aligned with a principal stream direction of processed liquid which passes through said container. In the liquid processing device, processed liquid passes into the arrangement of pieces. Therefore, the liquid processing device can change the nature of the processed liquid more effectively.

In the preferred embodiment of the present invention, the liquid processing device may be connected to a service pipe to supply said liquid, and said liquid is pressurized comparing with surrounding atmospheric pressure in said pipe. Because the intake and the outlet of the liquid processing devise are connected directly into a service pipe of processed liquid, the processing operation becomes easy, and the processed liquid is supplied easily in a wide area.

The liquid that is pressurized comparing with atmospheric pressure includes, for example:

tap water pressurized at water purification plants;

well water which it is pumped up to a water tower, and is pressurized by gravity;

beverage stationed in a tank, and pressurized by gravity; and fuel (including gasoline, light oil, fuel alcohol) of an internal combustion engine pressurized by a fuel pump.

(Processed Liquid)

Liquid being passed through the liquid processing device is explained. The liquid includes solution, suspension, colloid solution, mixture with liquid and particles. Also, the liquid includes one passed a single time through the liquid processing device and one passed through multiple times. Multiple times passage processing may be done by repeating single time processing, or by making a closed flow path intervened with the device, and circulating the liquid therein.

An example of the liquid is a beverage of which taste is varied in comparison with before processing. Another example is water with suppressed microorganism's propagation resulting from the processing.

The liquid may be water. The water includes drinking water for human beings and domestic animals, distilled water, and water for plant culture.

DETAILED DESCRIPTION OF THE PREFERRED EMBODIMENTS

The arrangement of pieces and the liquid processing device of the present invention are explained further, referring to figures. The description in the following embodiments, experiments and application examples, are mere illustration and does not limit the scope of the present invention in any manner, such as dimensions of parts and members, materials, shape, and relative positions, unless it is specifically mentioned otherwise.

Example 1 of the Embodiment

Figure 3:
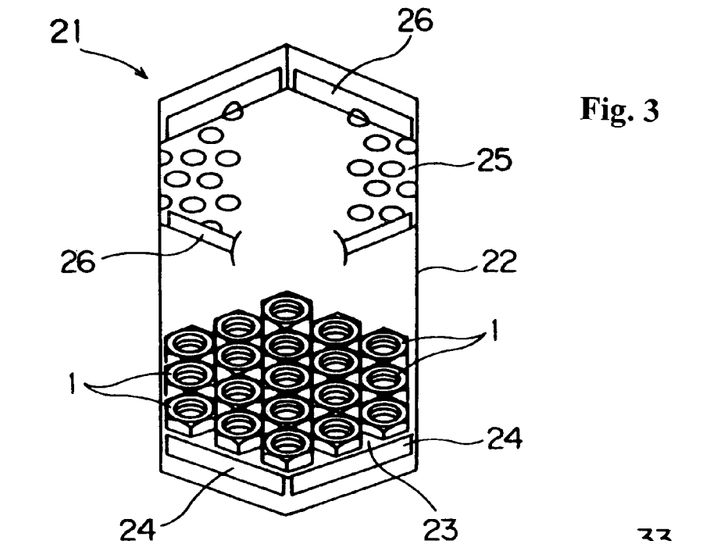
FIG. 3 is a partially cutaway perspective view of the arrangement of pieces (1).

FIG. 3 is a partially cutaway perspective view of the arrangement of pieces (1). In FIG. 3, plural 1 represent material pieces, 22 represents an equilateral hexagonal prism shaped hollow case, 23 represents a bottom plate and 25 represents a top plate.

The material pieces 1 have an external shape of an equilateral hexagonal prism, of which length of one side (l) is 3 mm, height (h) is 2.4 mm, and diameter of a hole is 3 mm. The hole's position is in the center of the equilateral hexagonal prism and has the shape of a normal circular prism. A spiral groove of the internal perimeter surface of the hole is meter coarse screw thread. Material of the material piece 1 is SUS304. The material pieces are oriented after heat-treating and cooling.

The case 22, the bottom plate 23 and the top plate 25 are made of a thin board of SUS304. The bottom plate 23 and the top plate 25, have many through holes of a diameter of 3 mm. A part of the through holes of the top plate 25 is omitted in the figure.

A peripheral portion 24 of the bottom plate 23 is bent and that is secured to a base part of the case 22 by welding in part. Nineteen pieces of the material piece 1 are oriented as OHA on the bottom plate 24. These nineteen pieces compose one step, and nine steps thereof are piled up. (The second through ninth steps are not illustrated in the figure.) The total number of the material pieces 1 is one hundred seventy-one (171) pieces. OHA of each step piled up such that the centers of the concentric circles generally align. Therefore, the central axes 7 of the material pieces 1 oriented at the center in each step, form an imaginary approximately straight line.

A peripheral portion 26 of the top plate 25 is bent and that is secured to a top part of the case 22 by welding in part. As of the outside dimension of the case 22, one side length of the equilateral hexagonal prism is 15 mm, height is 31 mm and distance of the top plate 25 from the bottom plate 23 is 22 mm. In the case 22, nineteen (19) pieces of the material piece is received in the arrangement of OHA. The second step to the nineteenth step is the same. By securing the arm side cover, the bottom plate 23 and the top plate 25, movement of the material pieces 1 are hindered, so that the arrangement is retained.

The arrangement of pieces 1 is placed in an air tight container, in the shape of an equilateral hexagonal prism (hereinafter called the arrangement of pieces (2)), and is employed in the application example mentioned below. Material of the airtight container is SUS304.

Example 2 of the Embodiment

Figure 4:
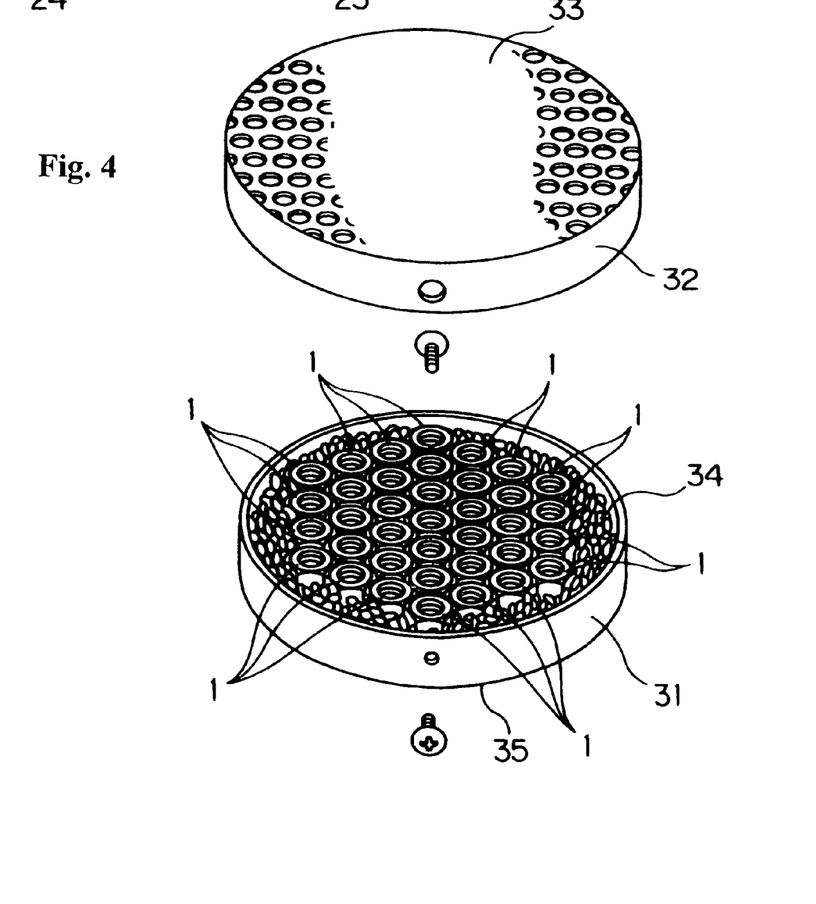
FIG. 4 is a perspective view of the arrangement of pieces (3).

FIG. 4 is a perspective view of the arrangement of pieces (3). In FIG. 4, 1 represent material pieces, 31 represents a cylindrical lower case and 32 represents a cylindrical top case.

The material, the size and the shape of material piece 1 are the same as the material pieces employed in arrangement of pieces (1). The material pieces are oriented after heat-treating and cooling.

The lower case 31 and the top case 32 are made of a thin board of SUS304. A bottom plate 35 of the lower case 31 and a top plate 33 of the top case 32, have many through holes of a diameter of 3 mm. A part of the through holes of the top plate 33 is omitted in the figure.

In the lower case 31, thirty-seven (37) pieces of the material piece 1 are oriented as OHA. These thirty-seven (37) pieces compose one step, and three steps thereof are piled up. The total number of the material pieces 1 is one hundred eleven (111) pieces. Only the third step appears in the figure. OHA of each step is stacked up such that the center of the concentric circle generally aligns. Therefore, the central axes 7 of the material piece 1 oriented at the center in each step, form an imaginary approximately straight line.

The top case 32 is fitted into the lower case 31 and secured by screwing screw bolts to the screw holes that are formed on the case side. 34 represent filler made by SUS304. The filler is filled with a gap between the arm side cover of the lower case 31 and the material pieces 1. The outside dimensions of the lower case 33, are diameter 63 mm and height 9 mm. Movement of the material pieces 1 are hindered by the arrangement of the arm side cover of the lower case, the filler 34, the bottom plate 35 and the top plate 33, so the above-mentioned arrangement of the material pieces 1 is retained.

The arrangement of pieces (3) as it is or positioned in a container, is used as the arrangement of pieces. In addition, it may be housed in a hollow container, and employed as a liquid processing device.

Example 3 of the Embodiment

Figure 5:
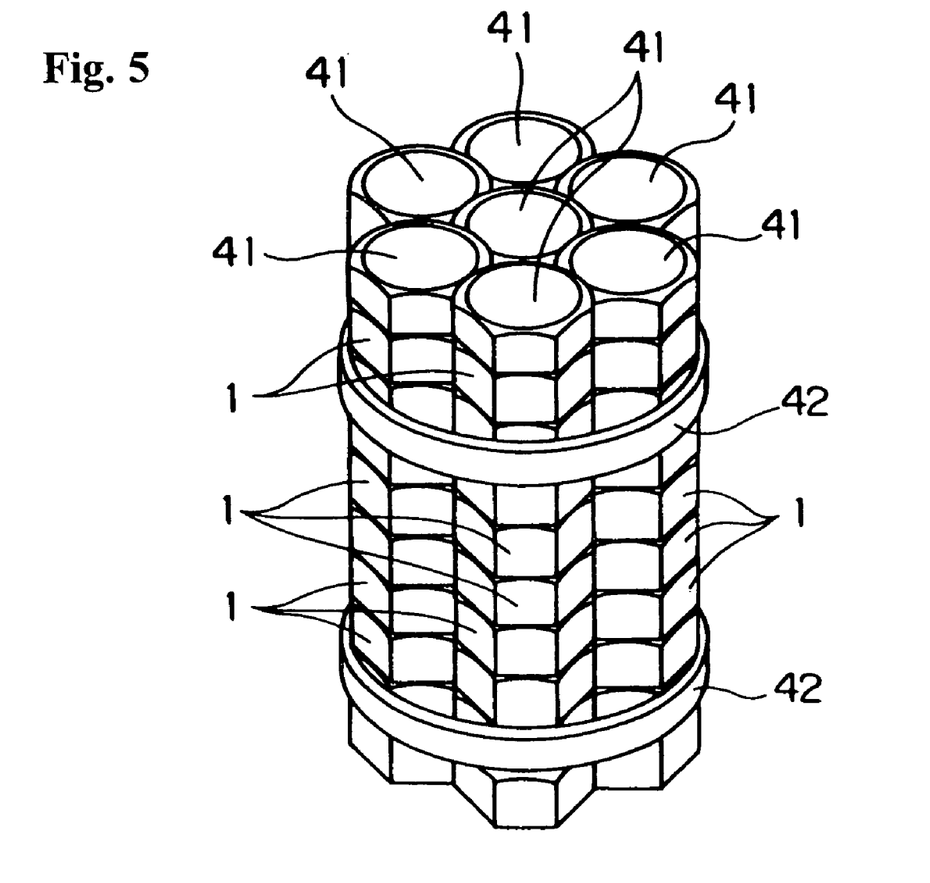
FIG. 5 is a perspective view of the arrangement of pieces (4).

FIG. 5 is a perspective view of the arrangement of pieces (4).

The material piece 1 has an external shape of an equilateral hexagonal prism, of which length of one side (l) is 5 mm, height (h) is 3.8 mm, and diameter of a hole is 5 mm. The hole is positioned in the center of equilateral hexagonal prism and has the shape of a normal circular prism. A spiral groove of the internal perimeter surface of the hole is meter coarse screw thread. Material of the material piece 1 is SUS304. The material pieces are oriented after heat-treating and cooling.

In the figure, 41 represents a bolt that has long leg and of which head shape is six angles. The bolt 41 is made of SUS304. A spiral groove of material piece 1 is threadingly engaged to the bolt 41. Thus, nine (9) material pieces are secured to the one bolt 41.

The seven (7) bolts that threadingly engaged the material pieces 1 are oriented in order that bases of each material piece make imaginary one plane and are bundled and fixed together with tying bands 42. The total number of the material pieces 1 is sixty-three (63) pieces. The tying bands 42 are made of synthetic resin, sold commercially.

The arrangement of pieces 4 shown in FIG. 5 is placed in an air tight container, the shape of which is an equilateral hexagonal prism (hereinafter called the arrangement of pieces (5)), and is employed in the application example mentioned below. Material of the airtight container is SUS304.

Further, the seven (7) bolts may be oriented such that the bases of each material piece are uneven in relation to each other. In this case, a drawing line linked projected points, which are caused that the central axes of the six (6) bolts located circumference are projected on an imaginative plane that is parallel to the bases of the material pieces, forms an equilateral hexagon.

Material of bolt 41 does not have any limit in particular, and may be made of any material such as synthetic resin, wood and the like. In addition, the shape of the head of the bolts 41 does not have any limit in particular. Thus, bolts having arbitrary head shape such as equilateral hexagon, circle, quadrangle and the like can be employed.

Example 4 of the Embodiment

Figure 6:
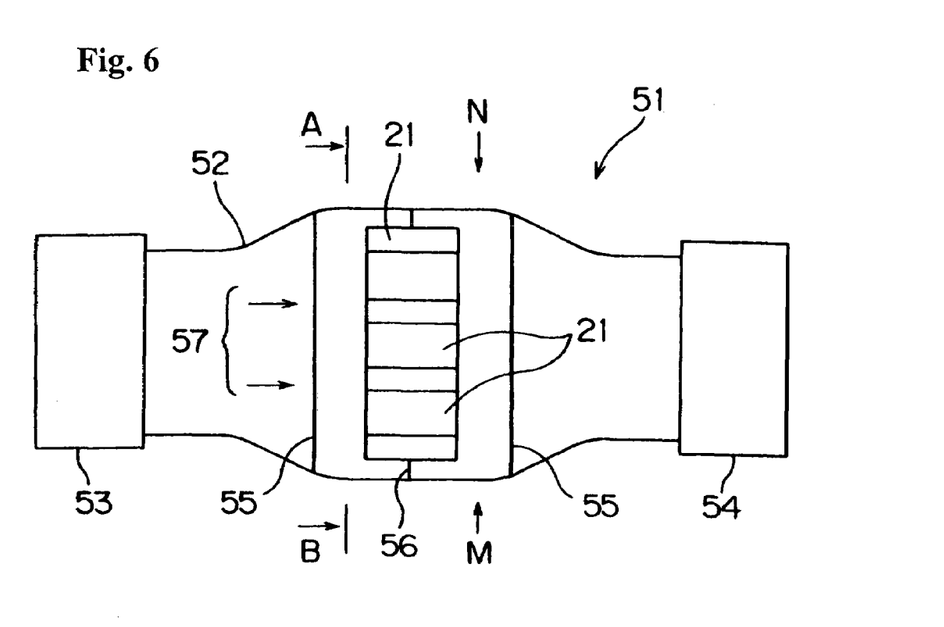
FIG. 6 is a sectional view of the liquid processing device.
Figure 7:
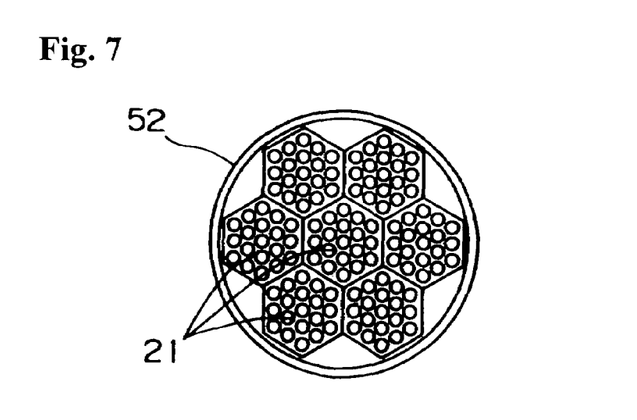
FIG. 7 is a sectional view taken on line A-B of FIG. 6.

FIG. 6 is a sectional view of the liquid processing device. FIG. 7 is a sectional view taken on line A-B of FIG. 6.

Liquid processing device 51 is a device wherein the arrangement of pieces (1) 21 is installed inside of a hollow column 52. In the figure, 53 represents a socket and 54 represents a socket. The socket 53 is for intake of fluid and the socket 54 is for outlet of fluid. A section taken on line A-B in FIG. 6 is shown in FIG. 7. Seven (7) of the arrangements of pieces (1) 21 are installed in the inside of the column 52. An arrow 57 represents direction of stream line of processed fluid, and such direction generally aligns with a direction of central axis of the material pieces 1 in the arrangement of pieces (1). 55 represent riddle boards that have many through holes of diameter of 3 mm. The riddle boards 55 are placed at an upstream side and a downstream side of the arrangement of pieces (1) 21, for each one piece respectively. Material of the column 52, the sockets 53, 54 and the riddle boards 55 are SUS304.

The cases of the seven (7) arrangements of pieces (1) are welded to each other so that they are secured as OHA. The cases are then linked to an inner wall of column 52 by welding at point 56. The liquid processing device 51 consists of two cylindrical segments, after having secured the arrangements of pieces (1) 21 and the riddle board 55 to the two segments, the two segments are integrated at section N-M, by welding. In addition, the two segments may be integrated in the following manner. At the joining ends of the two cylindrical segments, screws are engraved and tightened accordingly.

The greatest diameter of the column 52 is 90 mm. On internal perimeter surfaces of socket 53, 53, screws are engraved, which can tighten to a water supply pipe.

The liquid processing device 51 can be intervened directly to a service pipe such a tap water and well water supply pipe that supplies well water being pumped up to a water tower and is pressurized by gravity. Namely, cutting the water supply pipe, an upstream end of the cut pipe is connected to the socket 53, and a downstream end of the cut pipe is connected to the socket 54. The sockets 53, 54 fit water supply pipe having a diameter of 50 mm. The liquid processing device 51 can alter water passing through the water supply pipe having a diameter of 50 mm.

Processing object of the liquid processing device 51 is liquid. Examples of such liquid are drinking water, vegetables juice, fruit juice, and other beverage. By passing citrus juice through the liquid processing device, a change of the taste occurs. Specifically, decreased acidity was observed.

Example

Capability of the arrangement of pieces was examined changing size and materials of the material piece 1.

The experiment was carried out using 4 kinds of material piece of SUS304 and 1 material piece of titanium. The external shape of the material pieces was an equilateral hexagonal prism. The length of one side (1) and the diameter of the hole were equal. The material piece used had the hole positioned in the center of the equilateral hexagonal prism, having the shape of a normal circular prism, and having a spiral groove of meter coarse screw thread on the internal perimeter surface of the hole. The material pieces of SUS304 were employed for the experiment after heat-treatment and cooling. The material pieces of titanium having finished solution treatment were purchased.

On a wooden board, each of nineteen (19) pieces of the above mentioned material piece and also the material piece of SUS304 without heat-treating were oriented as OHA and contacted to each other to make one step. The same steps were stacked up one on top of the other to make three steps (total number of material pieces were fifty-seven (57)). The central material piece of the concentric circle of each step, were aligned as well as the equilateral hexagon shape of each step. The material pieces were fixed temporarily.

As for the evaluation, sensory analysis whether taste of a sliced lemon changed or not was carried out. Namely, if a sliced lemon piece is left on an arrangement of pieces for several minutes, sour taste becomes weak, and bitter taste is emphasized. Therefore, slices lemon piece were left on the arrangement of the material pieces for 10 minutes. Three panelers examined change of the taste. ○ indicated that the taste was changed, x indicated that the taste was not changed. In addition, the taste change would appear strong, if lemon employed would be fresh lemon. Therefore, a fresh lemon having green color of its peel was employed for the examination. Experimental results are shown in Table 1.

TABLE 1

| Material | Example | | | | | Comparative Example |
|---|---|---|---|---|---|---|
| | SUS304 | | | | Titanium | SUS304 |
| Length of one side (l) mm | 6 | 5 | 4 | 3 | 4 | 3 |
| Height (h) mm | 4.5 | 3.8 | 3.1 | 2.4 | 3.1 | 2.4 |
| Paneler-1 | ○ | ○ | ○ | ○ | ○ | X |
| Paneler-2 | ○ | ○ | ○ | ○ | ○ | X |
| Paneler-3 | ○ | ○ | ○ | ○ | ○ | X |

A change of taste does not appear in the experiment for comparison that is without heat-treating.

Application Example 3

Liquid processing device was installed on water supply pipe of a hoggery. Such water was used for drinking water of hogs and for cleaning of pigpens, water quality of raw sewage that are mixed of hog waste and pigpen drainage was observed.

The hoggery that the experiment took place, located in Saikai-cho, Nagasaki prefecture. The lot was 40m×120m, the pigpen was 30m×100m, number of the total pigs is 500. Liquid processing device 51 was installed in the water supply pipe for sending water to the pigpen. The water was well water pumped up to a water tower, and pressurized. And the water that passed through the liquid processing device 51 was used for drinking water of hogs and for cleaning the pigpen.

The water sample, that was a mixture of hog waste and pigpen drainage was collected at the mouth of the septic tank. The measurement results of the sample water that just before the liquid processing device 51 was installed, and the sample water when 30 days after the liquid processing device 51 has been installed, are shown in Table 3.

TABLE 3

|  | Before installation | After installation |
|---|---|---|
| PH | 7.7 | 7.4 |
| BOD (mg/L) | 2440 | 1560 |
| COD (mg/L) | 1270 | 880 |
| SS (mg/L) | 1840 | 1100 |

As a result of having installed liquid processing device 51, water quality of raw sewage of the pigpen was improved.

Application Example 4

Placing arrangement of pieces and also installing liquid processing device on water supply pipe of hoggery, odor exhaled by hoggery was measured.

The hoggery that the experiment took place, located in Saikai-cho, Nagasaki prefecture. The lot was 40m×120m, the two pigpens were 30m×100m each, number of the total pigs is 300. Eight (8) arrangements of pieces (2) were placed in each pigpen at almost equal distance (the total number was 16). Also, on the same day placing the arrangement of pieces, the liquid processing device 51 was installed in the water supply pipe for sending water to the pigpens. The water was well water pumped up to a water tower, and pressurized. The water that passed through the liquid processing device 51 was used for drinking water of hogs and for cleaning the pigpens. Sample air was collected between the two pigpens, 110 days later from the day of placing the arrangements of pieces and installing the liquid processing device.

As a comparison object, a hoggery having similar scale and two pigpens, was chosen. At the almost same time of the same day, sample air for the comparison was collected between the two pigpens of the comparison object hoggery.

The assay of odor concentration carried out in sensory analysis by a three point comparison type smell bag method. For panelers, six people were chosen who have a normal sense of smell (the choice method for panelers used standard liquid smells).

One set of three smell bags bottled odorless air that passed activated charcoal and sealed. An appropriate amount of the collected sample air was added into one of the three smell bags. The same number of the above-mentioned set of the three smell bags as the number of panelers (6 sets) was made. The panelers (six people) smelled the three smell bags of one set respectively and chose the one bag that it seemed that the sample gas was added. The sensory analysis was continued as the sample air was diluted, till the average accuracy rate of the whole panel became less than 0.58.

The measurement results are shown in Table 4.

TABLE 4

|  | Installed hoggery | Comparative hoggery | Means of hoggery (number of measurements: 32) |
|---|---|---|---|
| Odor concentration | 12 | 100 | 79 |

Here, odor concentration means the dilution multiple that sample air was diluted with odorless clean air till having no odor. Bad smell of the hoggery decreased by placing the arrangement of pieces, also installing the liquid processing device to water supply pipe of the hoggery and given the treated water as water to drink.

Application Example 3

An evaluation examination of sterilization power of the water that passed through the liquid processing device was carried out.

Examined water is the processed tap water that passed through the liquid processing device 51 and passed through activated charcoal in order to remove chlorine. 0.1 ml of fungus liquid having viable cell count $10^7$/ml were inoculated into 10 ml of the processed water, and incubated at 20° C. The viable cell was counted after 1 hour and 3 hours from the inoculation. The viable cell was counted by the way that an appropriate amount of the inoculated water was scattered into culture medium, and cultured, the number of produced colony were counted. In addition, as a control, 0.1 ml of fungus liquid were inoculated into 10 ml of phosphate buffer ($1/15$M, pH7.2), and incubated in a like manner. The viable cells were counted after the same time course.

The bacteria employed for the experiment were *Escherichia coli*, *Staphylococcus aureus*, *Legionella pneumophilia*, and *Salmonella enteritidis*. The culture medium employed in the count of viable cell was standard agar medium (Eiken) and GVPC a agar medium (Nikkenn seibutu). The viable cell count at the beginning calculated by one of the colony culture examination. The viable cell count after 1 hour and 3 hour from the inoculation was calculated by the means of three of the colony culture examination.

Examination results are shown in Table 5.

TABLE 5

|  |  | After 1 hour | | After 3 hours | |
|---|---|---|---|---|---|
|  | At the beginning | Processed water | Control | Processed water | Control |
| *E. coli* | $4.9 \times 10^5$ | $3.1 \times 10^5$ | $5.6 \times 10^5$ | $2.1 \times 10^5$ | $5.8 \times 10^5$ |
| *St. aureus* | $4.8 \times 10^5$ | $3.9 \times 10^5$ | $4.6 \times 10^5$ | $1.6 \times 10^5$ | $4.4 \times 10^5$ |
| *Leg. pneumophila* | $5.6 \times 10^5$ | $3.5 \times 10^5$ | $5.6 \times 10^5$ | $1.4 \times 10^5$ | $5.4 \times 10^5$ |
| *Sal. enteritidis* | $4.7 \times 10^5$ | $1.6 \times 10^5$ | $4.4 \times 10^5$ | $5.2 \times 10^3$ | $4.4 \times 10^5$ |

(Unit: CFU/ml)

The tap water that passed the fluid processing device showed sterilization ability against the 4 species of bacteria. Particularly, *Salmonella enteritidis* decreased to about 1% after 3 hours.

Application Example 4

A hydroponics examination of a plant was carried out in the tap water that passed through liquid processing device.

Leaves of Angelica keiskei were employed for the examination. The tap water that passed through the liquid processing device 51 and tap water without passing through were poured in separate vessels.

A leaf of Angelica keiskei was cut from the base of a leafstalk. The leaf stalk parts were put in the vessels. They were placed in the same place. The changes were observed.

The leaf put in the tap water that passed through the liquid processing device 51, has still kept green after 45 days elapsed. On the other hand, the leaf put in the tap water without passing through, withered in 2 days.

INDUSTRIAL APPLICABILITY

The liquid processing device of the present invention can be used for conversion of drinking water of hogs, and reduction of bad smell at hoggery, installing it in water supply pipe of a hoggery.

The liquid of the present invention can be used for drink and for sterilization.

The invention claimed is:

1. A liquid processing device comprising,
a container having an intake and an outlet, and
heat-treated material pieces provided within said container, said material pieces each having an external shape of an equilateral hexagonal prism, and said material pieces each having a hole of an annular section penetrating through a base and a top thereof;
an internal surface of said hole having a spiral groove;
a material of said material piece being selected from the group consisting of austenitic stainless steel, martensitic stainless steel;
a casing securely fixing the material pieces in an arrangement and said casing having openings in a top plate and a bottom plate corresponding to said holes of the material pieces;
said arrangement being such that central axes of the material pieces are parallel to each other; wherein said central axes of each is an axis which is parallel to six sides of said equilateral hexagonal prism and perpendicular to said base and said top thereof;
wherein said arrangement is one such that said material pieces form a second equilateral hexagonal prism within said casings and said holes in the material pieces and openings in the casing are aligned;
wherein said material pieces within said casing are positioned in said container between the intake and outlet.

2. The liquid processing device as defined in claim 1, wherein,
said material pieces have identical shape and identical size to each other,
said hole having a circular prism shape, a central axis of said hole is identical with said central axis of said material piece, and
said arrangement is one such that said bases of said material pieces makes a plane and said sides of said material pieces are adjacent to each other.

3. The liquid processing device as defined in claim 1, wherein said material pieces are piled one on top of the other within said casing.

4. The liquid processing device as defined in claim 1 further comprising a plurality of said casings, wherein, said casings are piled one on top of the other, and
the central axes of the central material pieces within the plurality of casings are generally aligned.

5. The liquid processing device as defined in claim 1, wherein, material of said material piece is SUS304 stainless steel.

6. The liquid processing device as defined in claim 1, wherein,
a length of the side of said equilateral hexagon being designated as a cross section of said equilateral hexagonal prism of said material piece, is equal to or less than 10 mm, and
a height of said equilateral hexagonal prism is shorter than said length of said side.

7. The liquid processing device as defined in claim 1, wherein,
said spiral groove of said internal perimeter surface of said hole of said material piece, has a triangular screw thread shape.

8. The liquid processing device as defined in claim 1, wherein the container is SUS304 stainless steel.

9. A liquid processing device as defined in claim 1, wherein,
said openings in said casing are generally aligned with a principal stream direction of processed fluid which pass through said container.

10. A liquid processing device as defined in claim 9, wherein,
said liquid processing device is connected to a service pipe to supply said liquid, and said liquid is pressurized comparing with surrounding atmospheric pressure in said pipe.

* * * * *